United States Patent
Xiao

(10) Patent No.: US 12,264,302 B2
(45) Date of Patent: Apr. 1, 2025

(54) PROCESS TO IMPROVE PROTEIN RECOVERY IN STILLAGE PROCESSING STREAMS

(71) Applicant: Ecolab USA Inc., St. Paul, MN (US)

(72) Inventor: Lan Xiao, Naperville, IL (US)

(73) Assignee: Ecolab USA Inc., St. Paul, MN (US)

( * ) Notice: Subject to any disclaimer, the term of this patent is extended or adjusted under 35 U.S.C. 154(b) by 1028 days.

(21) Appl. No.: 17/166,094

(22) Filed: Feb. 3, 2021

(65) Prior Publication Data

US 2021/0253984 A1    Aug. 19, 2021

Related U.S. Application Data

(60) Provisional application No. 62/976,921, filed on Feb. 14, 2020.

(51) Int. Cl.

| | |
|---|---|
| *C12F 3/10* | (2006.01) |
| *A23K 10/38* | (2016.01) |
| *B01D 21/00* | (2006.01) |
| *B01D 21/01* | (2006.01) |
| *C02F 1/24* | (2023.01) |
| *C02F 1/56* | (2023.01) |
| *C02F 101/32* | (2006.01) |
| *C02F 101/38* | (2006.01) |
| *C02F 103/32* | (2006.01) |
| *C12P 7/06* | (2006.01) |

(52) U.S. Cl.
CPC ............. *C12F 3/10* (2013.01); *A23K 10/38* (2016.05); *B01D 21/0084* (2013.01); *B01D 21/01* (2013.01); *C02F 1/24* (2013.01); *C02F 1/56* (2013.01); *C12P 7/06* (2013.01); *C02F 2101/32* (2013.01); *C02F 2101/38* (2013.01); *C02F 2103/32* (2013.01)

(58) Field of Classification Search
CPC ....... C12F 3/10; A23K 10/38; B01D 21/0084; B01D 21/01; C02F 1/24; C02F 1/56; C02F 2101/32; C02F 2101/38; C02F 2103/32; C12P 7/06; A23V 2002/00; A23V 2250/5482; A23V 2300/18; A23V 2300/40; Y02E 50/10; Y02P 60/87; A23J 1/005; A23J 1/12

USPC .......................................................... 426/624
See application file for complete search history.

(56) References Cited

U.S. PATENT DOCUMENTS

| | | |
|---|---|---|
| 4,869,829 A | 9/1989 | Casey |
| 6,132,625 A | 10/2000 | Moffett |
| 7,497,955 B2 | 3/2009 | Scheimann et al. |
| 7,582,215 B2 | 9/2009 | Hughes et al. |
| 9,051,538 B1 | 6/2015 | Roa-Espinosa |
| 9,516,891 B1 | 12/2016 | Roa-Espinosa |
| 9,776,105 B2 | 10/2017 | Collins et al. |
| 2006/0006116 A1 | 1/2006 | Scheimann et al. |
| 2012/0125859 A1* | 5/2012 | Collins ................ B01D 17/042 210/708 |
| 2015/0076078 A1 | 3/2015 | Gallop |
| 2016/0115425 A1* | 4/2016 | Blankenburg ....... B01D 17/047 554/20 |
| 2017/0015938 A1* | 1/2017 | Xiao ....................... C11B 13/00 |
| 2018/0071657 A1 | 3/2018 | Hale et al. |
| 2018/0273878 A1 | 9/2018 | Xiao et al. |

FOREIGN PATENT DOCUMENTS

| | | |
|---|---|---|
| RU | 2590600 | 7/2016 |
| WO | WO 2017/142827 A2 | 8/2017 |
| WO | WO 2020/168255 A1 | 8/2020 |

OTHER PUBLICATIONS

European Patent Office, International Search Report in International Patent Application No. PCT/US2021/016285, 8 pp, (May 20, 2021).
European Patent Office, Written Opinion in International Patent Application No. PCT/US2021/016285, 6 pp, (May 20, 2021).
U.S. Appl. No. 16/791,841, filed Feb. 14, 2020.

* cited by examiner

*Primary Examiner* — Bhaskar Mukhopadhyay
(74) *Attorney, Agent, or Firm* — Leydig, Voit & Mayer, Ltd.

(57) ABSTRACT

Provided is a method of processing stillage from an ethanol production process. The method comprises treating stillage comprising oil, protein, and water upstream of a separation, concentration or evaporation step with at least one organic coagulant and at least one flocculant, thereby forming treated thin stillage comprising solids which include at least a portion of the oil and protein; and clarifying the treated stillage via a solid/liquid separation process thereby forming clarified stillage and a separated solids phase comprising at least a portion of the protein from the stillage.

7 Claims, 10 Drawing Sheets

PROCESS TO IMPROVE PROTEIN RECOVERY IN STILLAGE PROCESSING STREAMS

CROSS-REFERENCE TO RELATED APPLICATIONS

This patent application claims the benefit of U.S. Provisional Patent Application No. 62/976,921, filed Feb. 14, 2020, which is incorporated by reference.

BACKGROUND OF THE INVENTION

Stillage process streams typically involve milling/grinding, further processing, separation, and recovery/separation of solids and oils from the stillage. For example, in a dry milling process for the manufacture of ethanol, corn is ground up and processed to produce a "beer mash" which is fermented to form ethanol. Once the stream reaches the desired ethanol content, the material is then transferred to a stripper column. The stripper column facilitates recovery and removal of the ethanol and the remaining stream, known as whole stillage, is passed on for further processing.

In ethanol production processes that involve dry milling of corn, for example, whole stillage contains non-fermentable components of the corn kernels including germ, protein, gluten, and fiber, as well as fats and oils and a small amount of starch, in addition to dead yeast cells. Whole stillage typically contains 9%-14% total solids of which 4% to 10% are suspended solids and 4% to 5% are dissolved solids. Many of the components of whole stillage; i.e., oil and protein solids, are useful, and considerable attention has been devoted in the industry to develop methods to separate and recover those components.

Typically, various uses of heat and centrifuge pressures are applied to whole stillage, thin stillage, or syrup to recover at least some of these components. Typical prior art processes involve centrifuging away water from the whole stillage thereby forming a wet cake of concentrated solids and a thin stillage stream that is low in solids. The thin stillage then undergoes some form of drying or evaporation to form a viscous syrup. Part of the thin stillage stream may be reused in the process by recirculating to the front of the plant as backset and mixing it with new corn. The syrup is typically added to other solids recovered from the process to form a mass commonly known as Distiller Dry Grains and Solubles (DDGS), which can be used, for example, as an animal feed.

U.S. Pat. Nos. 9,051,538 and 9,516,891 disclose a multistage process for the separation of bio-components from a waste stream containing DDGS, in which the waste stream is separated into a stream containing predominantly protein, a stream containing predominantly oil, a stream containing predominantly water, and a stream that contains predominantly fibers, by using polymers and separation equipment including a plate separator, a press and a dissolved air floatation device. U.S. Pat. No. 7,497,955 discloses a method of dewatering thin stillage process streams by adding to the process streams an anionic flocculating amount of an anionic copolymer comprising a monomer unit derived from acrylic acid. U.S. Pat. No. 9,776,105 discloses a method of treating thin stillage upstream of a concentration or evaporation step with an inverse emulsion containing an anionic flocculant and an emulsifying agent.

There is a clear need and utility for improved methods, systems, and apparatus for improving clarification of ethanol stillage and generating DDGS product with enriched protein content, while maintaining or improving oil recovery from the stillage.

BRIEF SUMMARY OF THE INVENTION

The invention provides a method recovering protein from stillage produced in an ethanol production process, which method involves treating stillage comprising oil, protein, and water upstream of a separation, concentration or evaporation step with at least one organic coagulant and at least one flocculant, to produce a treated stillage comprising solids which include at least a portion of the oil and protein; and clarifying the treated stillage via a solid/liquid separation process, to produce a clarified stillage comprising a clarified aqueous phase and a separated solids phase, wherein the separated solids phase comprises at least a portion of the protein in the stillage. In some embodiments, the separated solids phase may be in the form of a float layer, e.g., obtained in a process for producing ethanol from dry milled/dry ground corn.

The method of the invention can be applied to any suitable stillage process for producing ethanol. For example, the method of the invention may be applied to stillage processes in which the ethanol is produced in an ethanol biofuel plant, a spirits distillery, or a brewery or the like. The method of the invention may be applied in ethanol production processes that use a wet milling process or a dry grind process.

The method of the invention may be used in the treatment of either whole stillage or thin stillage.

In the method of the invention, the coagulant preferably includes one or more organic coagulants. The flocculant may include, e.g., an anionic flocculant. The solid/liquid separation process may include, e.g., dissolved air flotation, induced air flotation, or a combination thereof.

In some embodiments, the method of the invention further includes separating at least a portion of the oil from the separated solids phase, e.g., from a float layer, to produce a de-oiled separated solids phase, e.g., a de-oiled float. The de-oiled separated solids phase produced according to the invention may be processed further, e.g., by drying and/or other treatment methods, to produce dry grains enriched for protein such as, e.g., protein-enriched distiller dry grain.

The present invention further provides an ethanol production process which utilizes the present inventive method of processing stillage produced in the ethanol production process.

The present invention also provides dried and/or dry grains, e.g., distiller dry grain with enriched in protein. The invention further provides a nutritional product comprising the dried/dry grains of the invention, e.g., distiller dry grain enriched in protein and produced according to the method of the invention, as well as a livestock feed or fertilizer comprising the dried/dry grains of the invention, e.g., distiller dry grain enriched in protein and produced according to the method of the invention. The invention further provides livestock feed or fertilizer comprising the dried/dry grains produced according to the present invention, wherein the livestock feed or fertilizer may further comprise biological sludge or other nutrients.

BRIEF DESCRIPTION OF THE SEVERAL VIEWS OF THE DRAWING(S)

DETAILED DESCRIPTION OF THE INVENTION

Figure 1:
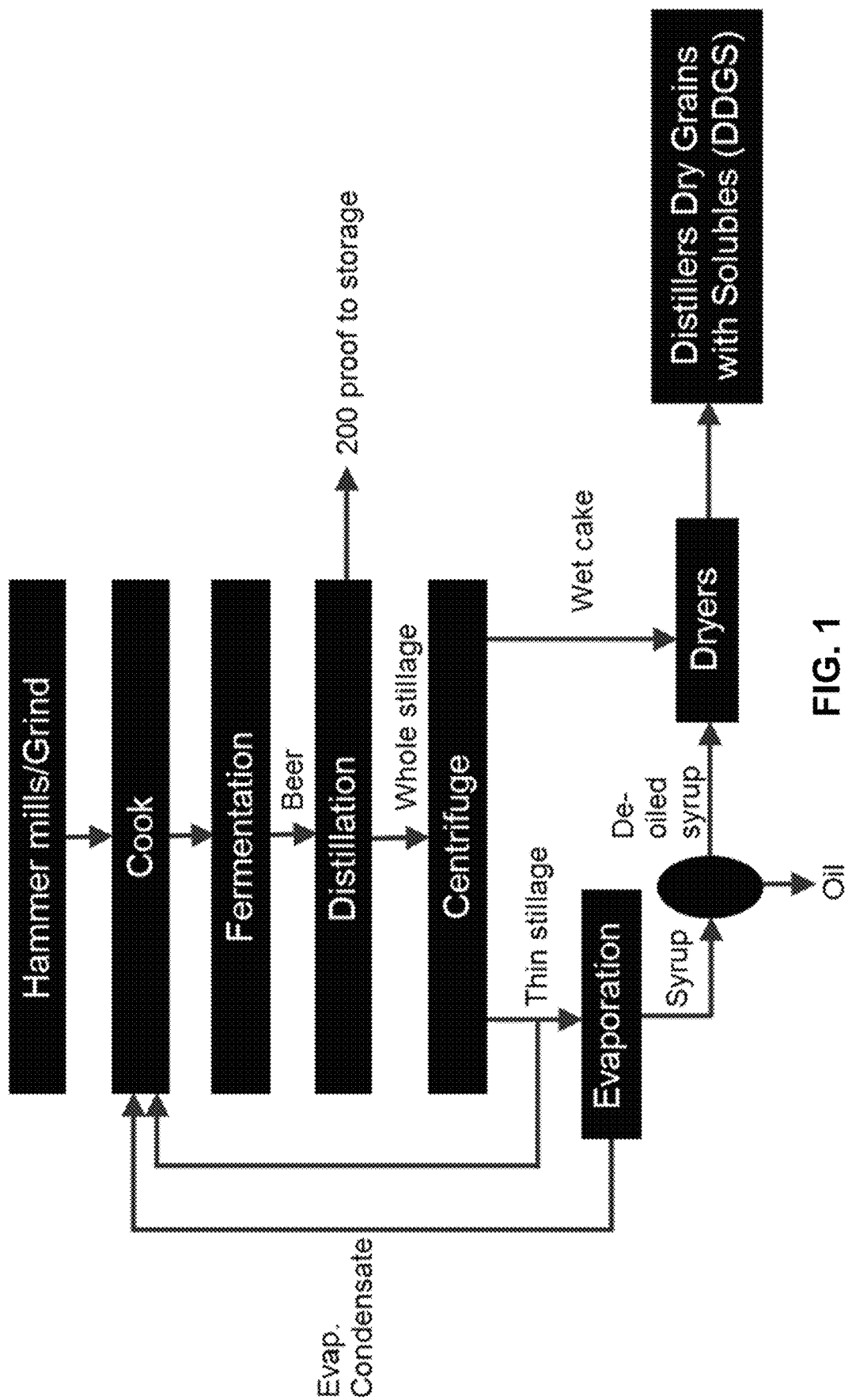
FIG. 1 depicts a flowchart illustrating a conventional method of processing stillage in a dry grind biofuel ethanol production process.
Figure 2:
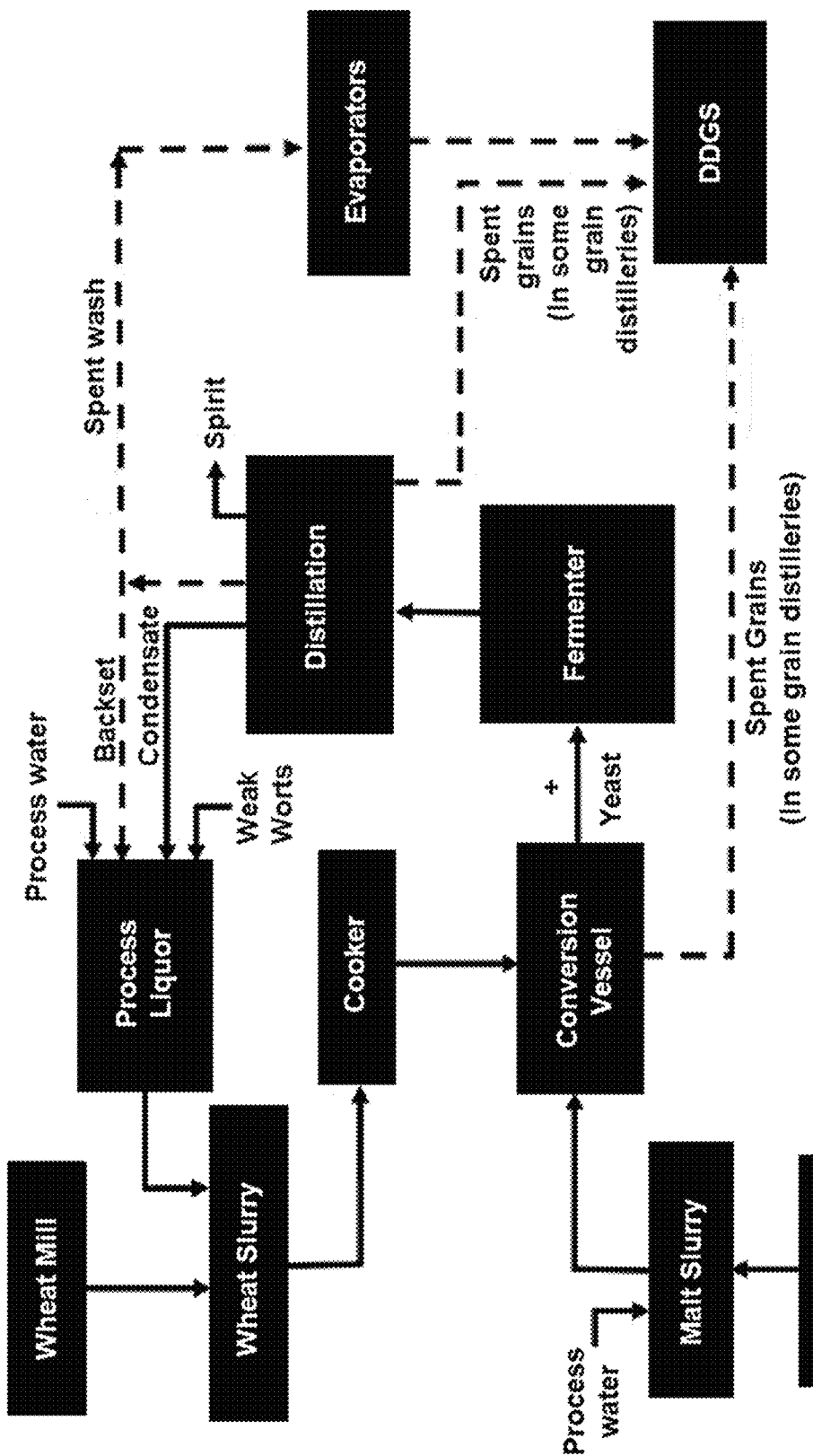
FIG. 2 depicts a flowchart illustrating a conventional method of processing stillage in a spirits distillery, e.g., a scotch whisky production process.
Figure 3:
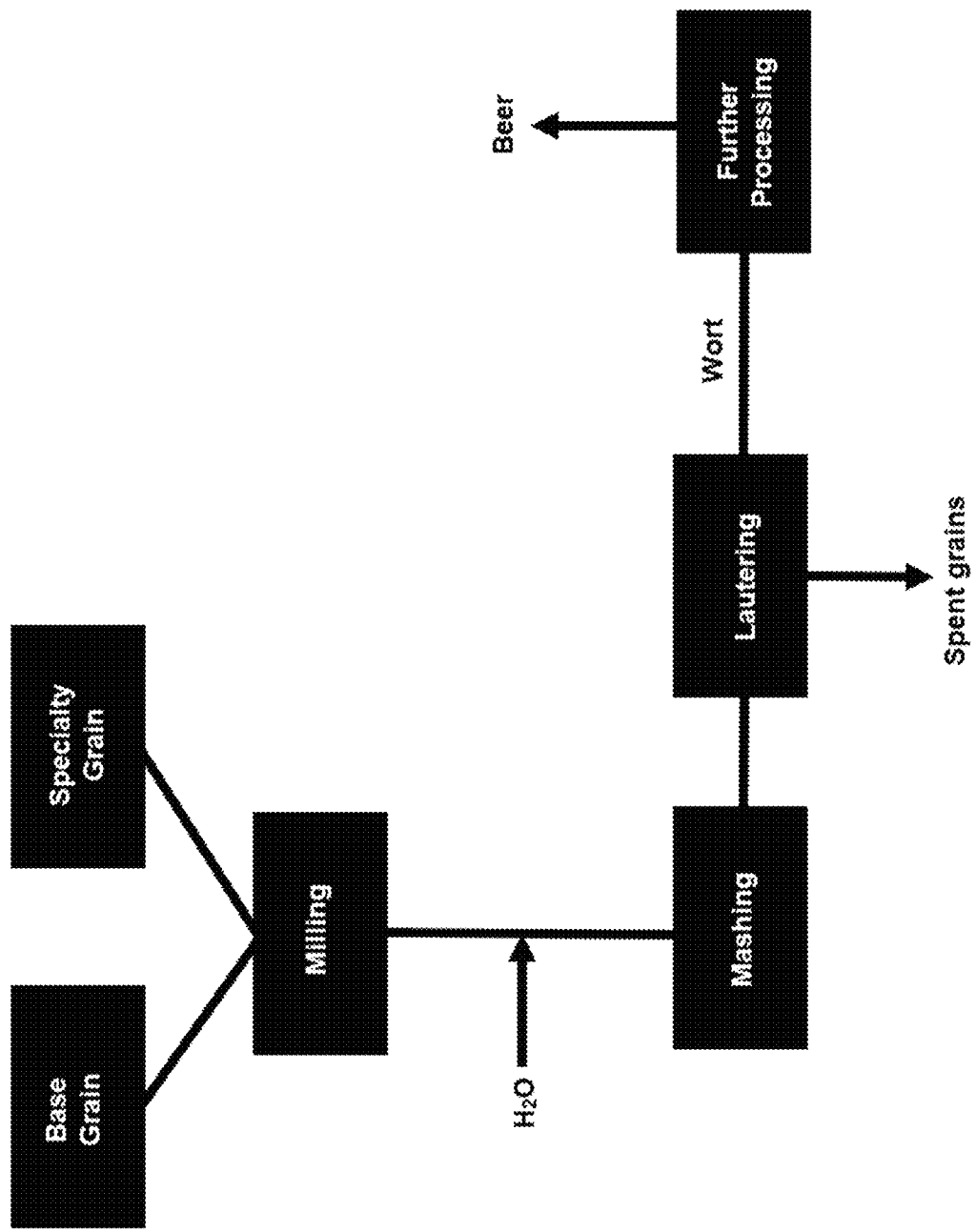
FIG. 3 depicts a flowchart illustrating a conventional method of processing stillage in a brewery production process.

As illustrated in FIG. 1, conventional processing requirements using mechanical means to extract the various products of a dry milling stillage process stream has disadvantages, among them high capital costs and high energy costs. In addition, the amount of the various products (protein, oil) that can conventionally be recovered from stillage with mechanical means is limited.

Figure 4:
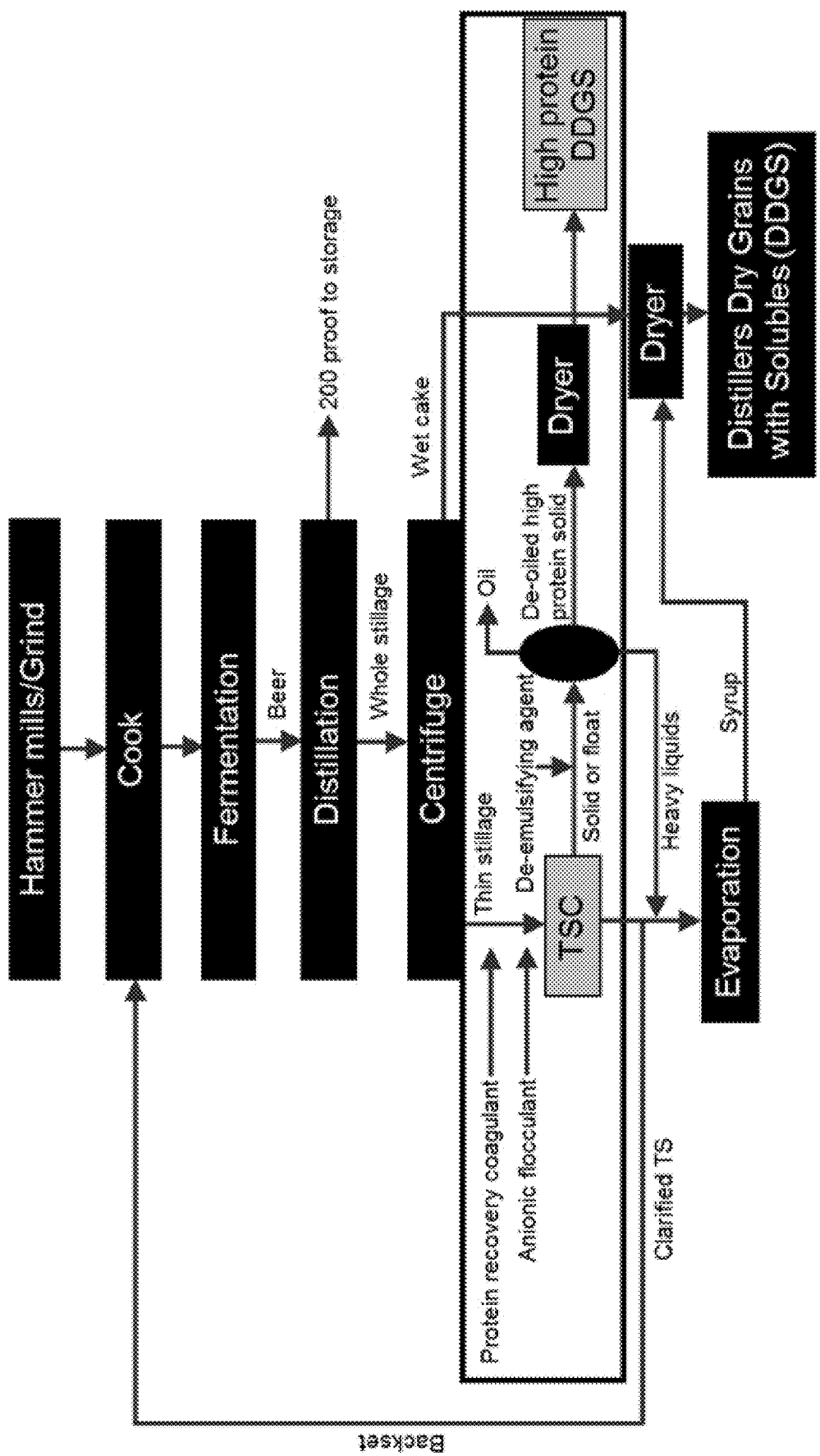
FIG. 4 depicts a flowchart illustrating one manner of implementing the method of the present invention in a dry grind biofuel ethanol production process.

The present invention provides an improved method of recovering protein from stillage produced in an ethanol production process, which includes treating stillage comprising oil, protein, and water upstream of a separation, concentration or evaporation step with at least one organic coagulant and at least one flocculant, to produce a treated stillage containing solids (e.g., coagulated and/or flocculated solids) which include at least a portion of the oil and protein; and clarifying the treated stillage via a solid/liquid separation process, to produce a clarified stillage containing a clarified aqueous phase and a separated solids phase, which in some embodiments may be in the form of a float layer, comprising at least a portion of the protein from the stillage. A flowchart illustrating one manner of implementing the inventive method in a dry grind biofuel process is shown in FIG. 4.

In some embodiments, the method of the invention may be used in processing whole stillage, thin stillage, or a combination thereof in a dry grind biofuel process or a spirits distillery. In one embodiment, the method of the present invention is used for processing thin stillage.

In some embodiments, the method of the invention further includes separating at least a portion of the oil from the separated solids phase, e.g., from a float layer obtained in a dry grind biofuel process, to produce a de-oiled separated solids phase, e.g., a de-oiled float layer. In accordance with some embodiments, the de-oiled separated solids phase, e.g., the de-oiled float layer, may be further processed, e.g., by drying and/or other treatment methods, to produce dry grains comprising protein, e.g., distiller dry grain comprising higher quality protein.

The coagulant preferably includes one or more chemical species that induce coagulation, i.e., the initial agglomeration of material suspended within a liquid. In the method of the invention, the coagulant may include one or more organic coagulants. In some embodiments, the coagulant consists exclusively of one or more organic coagulants in which case no inorganic coagulant is used. The organic coagulant may include one or more water-soluble polyelectrolytes or amine-based polyelectrolytes. Examples of suitable organic coagulants include poly(diallyldimethylammonium chloride) (polyDADMAC), epichlorohydrin-diethylamine, dimethylamine, polyamines, polyquaternary amines, or a combination thereof. In some embodiments, the organic coagulants are poly(diallyldimethylammonium chloride) (polyDADMAC), epichlorohydrin-diethylamine, or a combination thereof. These organic coagulants may be obtained commercially from Nalco Company, Naperville, IL as GR-308 and GR-305, respectively.

Generally, the coagulant may be added to the stillage process stream at a dosage sufficient to provide concentration of coagulant in the stillage of about 10 to about 1,000 ppm (based on the volume of stillage), e.g., at a dosage of about 50 ppm to about 1,000 ppm, at a dosage of about 100 ppm to about 1,000 ppm, at a dosage of about 200 ppm to about 1,000 ppm, at a dosage of about 500 ppm to about 1,000 ppm, at a dosage of about 50 ppm to about 100 ppm, or at a dosage of about 50 ppm to about 500 ppm.

In accordance with the present invention, if desired, coagulation and/or settling can be aided by the use of microparticulates. "Microparticulates" generally refer to certain insoluble materials which may be added to the process stream to physically interact with the suspended solids, fats, oils and/or greases in the process stream in such a way as to facilitate the separation and removal of these components by physical interaction. Without being bound by any particular theory, it is believed that addition of these materials provides a surface area and sites where polymers can interact and bridge the suspended particles forming an agglomerated particle or a floc. The use of microparticles may result in a floc or agglomerated particle that is more resistant to mechanical shear and as a result may use a physical sweep floc mechanism to capture and remove suspended solids, fats, oils and greases from the water phase. Once the desired particle interactions are achieved, the microparticulates may facilitate the separation process by increasing the rate of solids settling. Representative microparticulates may include, e.g., bentonite clay, montmorillonite clay, particularly montmorillonite clay available from CETCO, Arlington Heights, Ill. under the tradename AltaFloc, microsand (80 mesh silica sand), colloidal silica, colloidal borosilicate, starch and the like, and combinations thereof.

"Colloidal silica" and "colloidal borosilicate" generally refer to a stable aqueous dispersion of silica particles, e.g., amorphous silica particles or borosilicate particles, e.g., amorphous borosilicate particles, respectively, having a suitable particle size, e.g., having a particle size of up to about 500 μm, e.g., up to about 100 μm, up to about 50 μm, up to about 10 μm, up to about 1 μm, up to about 500 nm, or up to about 100 nm. Colloidal silica and colloidal borosilicate may be manufactured from known materials such as sodium silicate or borosilicate and are commercially available, for example from Nalco Company, Naperville, Ill.

Examples of suitable microparticulates include bentonite, montmorillonite, microsand, colloidal silica and colloidal borosilicate, and combinations thereof.

The microparticulate may be added to the stillage process stream prior to or after addition of the any coagulant(s) or flocculant(s), e.g., at a dosage sufficient to provide a concentration of microparticles in the stillage of about 10 to about 1,000 ppm.

The flocculant may include one or more chemical species which induces flocculation, e.g., by enhancing agglomeration of material suspended within a liquid either alone or after coagulation when the liquid is stirred or otherwise mixed. In the method of the invention, the flocculant may include at least one anionic flocculant. The anionic flocculant preferably creates a concentrated solids layer containing oil and insoluble protein. This concentrated layer in turn may be separated using known oil/solid/water mechanical separation techniques such as decanter, tricanter and stacked disk centrifuges. In some embodiments of the invention, the mechanical processing is performed with a stacked disk centrifuge.

Anionic polymers suitable for use in the method of this invention may include, for example, polymers prepared by polymerizing acrylic acid sodium salt, methacrylic acid sodium salt, 2-acrylamido-2-methyl-1-propanesulfonic acid sodium salt, or a combination thereof, and optionally one or more acrylamide monomers, under free radical forming conditions using methods known in the art of polymer synthesis. Such anionic polymers are commercially available, for example from Nalco Company, Naperville, Ill.

In some embodiments, the anionic polymer is cross-linked with about 0.005 to about 10 ppm of one or more cross linking agents. Representative cross-linking agents include but are not limited to N,N-methylenebisacrylamide, N,N-methylenebismethacrylamide, triallylamine, triallyl ammonium salts, ethylene glycol dimethacrylate, diethylene glycol dimethacrylate, polyethylene glycol diacrylate, triethylene glycol dimethylacrylate, polyethylene glycol dimethacrylate, N-vinylacrylamide, N-methylallylacrylamide, glycidyl acrylate, acrolein, glyoxal, vinyltrialkoxysilanes and the like. In some embodiments, the cross-linking agent includes from N,N-methylenebisacrylamide, polydiethyleneglycoldimethacrylate, trimethylolpropane ethoxylate (x EO/y OH) tri(meth)acrylate, where x=1-20 and y=1-5, trimethylolpropane propoxylate (x EO/y OH) triacrylate, where x=1-3 and y=1-3, 2-hydroxyethylmethacrylate, or a combination thereof.

In some embodiments, the anionic polymer includes one or more of: dry polymers, emulsion polymers, inverse emulsion polymers, latex polymers, dispersion polymers, and mixtures thereof. The advantages of polymerizing water-soluble monomers as inverse emulsions include 1) low fluid viscosity can be maintained throughout the polymerization, permitting effective mixing and heat removal, 2) the products can be pumped, stored, and used easily since the products remain liquids, and 3) the polymer "actives" or "solids" level can be increased dramatically over simple solution polymers, which, for the high molecular weight flocculants, are limited to lower actives because of viscosity considerations. The inverse emulsion polymers may then be "inverted" or activated for use by releasing the polymer from the particles using shear, dilution, and, generally, another surfactant, which may or may not be a component of the inverse emulsion.

The inverse emulsion polymer may be prepared by dissolving the desired monomers in an aqueous phase, dissolving the emulsifying agent(s) in an oil phase, emulsifying the water phase in the oil phase to prepare a water-in-oil emulsion, in some cases, homogenizing the water-in-oil emulsion, polymerizing the monomers dissolved in the water phase of the water-in-oil emulsion to obtain the polymer as a water-in-oil emulsion. If desired, a self-inverting surfactant can be added after the polymerization is complete in order to obtain the water-in-oil self-inverting emulsion.

The oil phase may include one or more inert hydrophobic liquids. Examples of suitable hydrophobic liquids include aliphatic and aromatic hydrocarbon liquids such as, e.g., benzene, xylene, toluene, paraffin oil, mineral spirits, kerosene, naphtha, and the like. In some embodiments, the oil phase includes a paraffinic oil.

Water-in-oil emulsifying agents may be used for preparing the emulsion polymers useful in the method of the invention. Suitable emulsifying agents include sorbitan esters of fatty acids, ethoxylated sorbitan esters of fatty acids, and the like, or mixtures thereof. Preferred emulsifying agents include sorbitan monooleate, polyoxyethylene sorbitan monostearate, polyoxyethylene sorbitan monolaurate, and the like. The sorbitan can be substituted with sucrose, glycol, glycerin, and the like. Additional details on these agents may be found in McCutcheon's Detergents and Emulsifiers, North American Edition, 1980. Any inverting surfactant or inverting surfactant mixture described in the prior art may be used. The amount of emulsifying agent utilized may be varied in order to optimize polymer make down and also to improve separation and recovery of the fats oil and greases present in the process stream. While the use of latex flocculants may be preferred in some embodiments, it is also possible to feed one or more anionic flocculants, alone or in combination, with an additional point source feed of one of the surfactants in order to facilitate and/or optimize separation and recovery of oil from the float layer. Representative inverting surfactants include, e.g., ethoxylated nonylphenol, ethoxylated linear alcohols, and the like, and combinations thereof. In some embodiments, the inverting surfactant includes one or more ethoxylated linear alcohols.

Upon flocculant addition to, e.g., dry milling stillage process streams, these same emulsifying agents and/or surfactants may interact with the oil, e.g., corn oil, which is bound to the surfaces of the solid constituents of the stillage, or the emulsifying agents and/or surfactants may interact with the unattached oil present in these dry milling streams. This interaction enables the oil, e.g., corn oil, to break free from the solid surfaces and be removed by separation processes such as high speed centrifugation. These same surface active chemicals also may help emulsify unattached oil preventing attachment to solid material present in the stillage process streams, which also aids in the removal of oil from the stillage.

Dispersion polymers may be prepared by combining water, one or more inorganic salts, one or more water-soluble monomers, any polymerization additives such as chelants, pH buffers or chain transfer agents, and a water-soluble stabilizer polymer. Examples of suitable dispersion polymers and methods of preparing them may be found in U.S. Pat. No. 9,776,105. The advantages of preparing water-soluble polymers as water continuous dispersions are similar to those provided by inverse emulsion polymers. The water continuous dispersion polymers have the further advantages in that they contain no hydrocarbon oil or surfactants, and require no surfactant for "inversion" or activation.

Dry polymers suitable for use in the method of the invention include those described in U.S. Pat. No. 9,776,105.

In some embodiments, an anionic polymer is used which has an anionic charge of from about 10 to about 100 mole percent, e.g., from about 30 to about 70 mole percent, and more particularly with an anionic charge of about 35 to about 45 mole percent. In some embodiments of this invention, the anionic polymer includes an acrylamide-acrylic acid sodium salt copolymer, an acrylamide-2-acrylamido-2-methyl-1-propanesulfonic acid sodium salt copolymer, or a combination thereof. Examples of suitable anionic polymers include acrylamide-acrylic acid sodium salt copolymers and acrylamide-2-acrylamido-2-methyl-1-propanesulfonic acid sodium salt copolymer, one or both having a 25 anionic charge of about 10 to about 90 mole percent, and any combination thereof.

Emulsion polymers may be inverted as a 0.1 to 5.0 percent by weight solution in clean water according to standard practices for inverting latex flocculants as described herein. The polymer may be applied to the stillage or slop process stream. Dry anionic polymer flocculants may be used in a similar fashion with the product being made up at concentrations of 0.1 to 1.5 percent polymer product according to the standard practices and recommended polymer aging times for preparing dry flocculants.

In some embodiments, the anionic flocculant includes a polymer comprising a monomer unit derived from a monomer selected from 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid, salts thereof, and combinations thereof. In some embodiments, the anionic flocculant is a polymer comprising a monomer unit derived from acrylic acid. An exemplary anionic flocculant includes GR-109, a high molecular weight inverse-phase emulsion consisting of ~25% polymer solids of polyacrylamide/acrylate and marketed commercially by Nalco Company, Naperville, IL.

The effective dosage, addition point(s) and mode of addition of anionic polymer to the stillage process stream may be empirically determined to obtain a desired polymer/particle interaction and optimize the chemical treatment program performance. Generally, the anionic polymer may be added to the stillage process stream at a dosage providing a final concentration of the anionic polymer in the stillage of about 10 to about 1,000 ppm, e.g., at a dosage of about 50 ppm to about 1,000 ppm, at a dosage of about 100 ppm to about 1,000 ppm, at a dosage of about 200 ppm to about 1,000 ppm, at a dosage of about 500 ppm to about 1,000 ppm, at a dosage of about 50 ppm to about 100 ppm, or at a dosage of about 50 ppm to about 500 ppm. In some embodiments, the anionic polymer is added to the stillage in an amount sufficient to provide a concentration of anionic polymer in the stillage of from about 50 ppm to about 500 ppm.

In some embodiments, the coagulant and/or flocculant used is GRAS approved, meaning it satisfies the requirements for the United States' FDA category of compounds that are "Generally Recognized as Safe." Using coagulants and/or flocculants that are GRAS approved is advantageous in that they need not be removed in certain applications, and can be included in the distiller grains and be fed to livestock and/or other animals, when used within the dosage and application guidelines established for the particular product formulation.

In some embodiments, the method of the present invention produces a two phase product, wherein one phase is rich in solids such as proteins and one is predominantly water. In at least one other embodiment, the method of the invention produces a three phase product, wherein one phase is rich in insoluble materials such as solids and/or proteins, one is predominantly water, and one is predominantly oil. The formation of a free-standing oil layer may vastly reduce the cost of otherwise removing oil from either of the water or, in particular, the insoluble material phases.

In some embodiments, the method of the present invention reduces the energy required to process whole stillage, thin stillage, concentrated thin stillage and/or syrup by reducing the amount of suspended solids present within the stillage. Suspended solids distribute mass throughout the stillage and when the stillage undergoes shear forces in separation equipment, the suspended solids significantly increase the energy required to properly separate the suspended solids and remove water from the stillage. The method of the present invention accordingly reduces the energy required in the solids separation steps of any of the de-watering processes including centrifugation or filtration, and reduces the amount of energy required for removing water during concentration or evaporation. Thus, the method of the present invention allows an ethanol processing facility to process more stillage without additional energy or to process stillage faster without additional energy by reducing the shear energy requirements and improving unit operation and process efficiency when the suspended solids are removed from the stillage.

The method of the invention also advantageously allows the composition of the backset to be changed favorably by removing the suspended solids. In conventional methods, it is difficult to remove certain solid materials because they remain suspended in the stillage and return to the front of the plant within the backset. Industry tends to re-use backset because it allows otherwise escaped materials to be recaptured on subsequent processing. Also, backset liquid reduces the need for additional fresh water thus lowering water costs. However, suspended materials contained therein continually increase in concentration each time the backset is recaptured and, as a result, shear energy requirement perpetually increases. By removing suspended solids in accordance with the present invention, water savings can be achieved, solids do not escape, and shear forces do not invariably rise. By improving quality of the backset, the method of the present invention increases production yield, improves evaporator performance/efficiency, reduces evaporator fouling and increases evaporator throughput.

In some embodiments, the method of the present invention reduces the energy requirements of the system by reducing the energy needed to concentrate the stillage. In other embodiments, by improving the quality of the backset, the method of the present invention may facilitate and/or increase the efficiency of ethanol production. In yet other embodiments, the flocculant and coagulant facilitate the increased recovery of grain solids and oil, e.g. corn oil.

In the method of the invention, the treated stillage is clarified via a solid/liquid separation process, to produce a clarified stillage comprising a clarified aqueous phase and a separated solids phase, e.g., which may be in the form of a float layer. In accordance with the present invention, the treated stillage is clarified upstream, i.e., prior to, a separation, concentration, and/or evaporation step used in conventional processing of stillage from ethanol production. In at least one aspect of this invention, one or more microparticulate settling aids may be added to the stillage process stream. The stillage may be aged for a relatively short period of time (0.5 to about 10 hours). "Aged" refers to the time that the stillage is left to sit in contact with one or more aids before heat and pressure are applied to this stillage mixture.

Separation of the water from the coagulated and flocculated stillage solids may be accomplished using any means commonly used for solid/liquid separation, such as a settling tank. In at least one embodiment, the stillage solids, fats and oils are concentrated and recovered on a float layer using a DAF (dissolved air flotation unit), IAF (induced air flotation unit) or GEM (gas energy mixing unit). Other embodiments contemplated by this invention include the removal of stillage solids by other sold/liquid separation devices such as a centrifuge, a recessed chamber filter press, rotary drum vacuum filters, belt presses, vacuum filters, pressure filters or membrane filtration.

In some embodiments, the float layer produced according to the method of the invention, e.g., as applied in an ethanol biofuel plant, comprises at least about 25 wt. % protein on a dry solids basis, e.g., at least about 27 wt. % protein on a dry solids basis. In another embodiment, the float layer comprises at least about 30 wt. % protein on a dry solids basis. Thus, in some embodiments, the float produced according to the method of the invention, e.g., as applied in an ethanol biofuel plant, may comprise, e.g., about 25 wt. % protein, about 26 wt. % protein, about 27 wt. % protein, about 28 wt. % protein, about 29 wt. % protein, about 30 wt. % protein, about 31 wt. % protein, about 32 wt. % protein, about 33 wt. % protein, about 34 wt. % protein, or about 35 wt. % protein, or more, on a dry solids basis In some embodiments, the float layer produced according to the method of the invention, e.g., in an ethanol biofuel plant comprises less than about 75 wt. % non-proteinaceous matter on a dry solids basis, e.g., less than about 73 wt. % non-proteinaceous matter on a dry solids basis. In another embodiment, the float layer comprises less than about 70 wt. % non-proteinaceous matter, e.g., about 70% or less of non-proteinaceous matter, or about 65% or less of non-proteinaceous matter, on a dry solids basis.

In some embodiments of the present invention, the stillage processing further includes separating at least a portion of the oil from the separated solids phase, which may be in the form of, e.g., a float layer, to produce a de-oiled solids phase, e.g., a de-oiled float layer. Any suitable method may be used to separate at least a portion of the oil from the separated solids phase. In some embodiments, the separation process may include heating and mechanical processing. In at some embodiments, the temperature applied to the aged mixture is relatively low, for example from about 150° F. to about 220° F. While using such a low temperature would not ordinarily be expected to result in high oil yields, the method of the present invention unexpectedly has been found to produce high oil yields at such temperatures. The mechanical processing may be performed using known oil/solid/water separation techniques such as decanter, tricanter and stacked disk centrifuges. In some embodiments, the mechanical processing is performed with a stacked disk centrifuge.

In some embodiments, an aid is used to recover oil from the stillage by forming different phase layers. Suitable oil recovery aids may include water-in-oil emulsifying agents conventionally used as oil recovery aids such as, e.g., sorbitan esters of fatty acids, ethoxylated sorbitan esters of fatty acids, and the like, and mixtures thereof. Examples of suitable emulsifying agents include sorbitan monooleate, polyoxyethylene sorbitan monostearate, polyoxyethylene sorbitan monolaurate, and the like. The sorbitan may be substituted, e.g., with sucrose, glycol, glycerin, and the like. Examples of suitable agents may be found in McCutcheon's Detergents and Emulsifiers, North American Edition, 1980. The amount of emulsifying agent utilized may be varied in order to optimize polymer make down and also to improve separation and recovery of the fats, oil, and/or greases present in the process stream. In some embodiments, a conventional inverting surfactant or inverting surfactant mixture may be used. Representative inverting surfactants may include, e.g., ethoxylated nonylphenol, ethoxylated linear alcohols, and the like. In some embodiments, one or more ethoxylated linear alcohols are used.

In some embodiments, the oil recovery agents may include one or more surfactants such as, e.g., a propylene glycol ester, a polyglycol ester, a polyglycerol fatty ester blend, a polyglycerol oleate ester, a block copolymer of ethylene oxide-propylene oxide polymer, a vegetable oil, a vegetable oil ethoxylate, and combinations thereof.

In some embodiments, the oil recovery agent includes hydrophobic or hydrophilic silica compounds. In some embodiments, the oil recovery agent includes propylene glycol.

In some embodiments, the oil recovery agent is a combination or blend of two or more of the surfactants, and/or emulsifying agents, and/or other recovery agents described herein.

In at least one embodiment, the oil recovery agent includes at least one surfactant and at least one microparticulate comprising hydrophilic silica, and the like, e.g., as described in U.S. Patent Application Publication No. 2018/0273878. In at least one embodiment, the oil recovery agent includes a composition available from Nalco Company, Naperville, IL, such as, for example, a composition containing a propylene glycol ester, a hydrophobic silica, a polyglycol ester, a polyglycerol oleate ester, a polyethoxylate sorbitan, a polyethoxylate sorbitan ester, and the like, and combinations thereof, e.g., as described in U.S. Patent Application Publication No. 2018/0071657.

Suitable oil recovery agents also may include, for example, oil separation aids supplied by Applied Material Solutions ("AMS") of Elkhorn, Wisconsin (United States). Examples of suitable oil recovery agents may include oil separation aids supplied by AMS under product numbers 8111, 8112, and 8113. Suitable oil recovery agents may include, for example, compositions containing a blend of 75-95% polysorbate 80, 5-15% AMS hydrophobic precipitated silica, and ≤10% petroleum hydrocarbon; compositions containing a blend of 75-95% castor oil ethoxylate, 5-15% AMS hydrophobic precipitated silica, 10-30% vegetable oil, and ≤10% propylene glycol; and compositions containing a blend of 75-95% polysorbate 80, 5-15% AMS hydrophobic precipitated silica, and ≤10% PEG ester blend. In some embodiments, the oil recovery agent includes a blend of 75-95% castor oil ethoxylate which includes polyoxyl 35 castor oil or which includes a mixture of polyethylene glycol (polyoxyethylene) castor oil compounds containing from 2 to about 2000 ethylene glycol (oxyethylene) units, 5-15% AMS hydrophobic precipitated silica which includes polydimethylsiloxane treated silica or siliconized silica, 10-30% vegetable oil, and ≤10% propylene glycol.

The oil recovery agent preferably interacts with the oil, e.g., corn oil, which is either bound to the surfaces of the solid constituents of the stillage, or with the unattached oil present in these dry milling streams. This interaction enables the oil to break free from the solid surfaces and be removed by separation process such as high speed centrifugation. These same surface active chemicals also may help to emulsify unattached oil preventing attachment to solid material present in the stillage process streams which also aids in the removal of oil from the stillage.

Generally, the oil recovery agent may be added to the stillage process stream at a dosage sufficient to provide a final concentration of oil recovery agent in the stillage of from about 10 ppm to about 1,000 ppm, e.g., from about 50 ppm to about 1,000 ppm, from about 100 ppm to about 1,000 ppm, from about 200 ppm to about 1,000 ppm, from about 500 ppm to about 1,000 ppm, from about 50 ppm to about 100 ppm, or from about 50 ppm to about 500 ppm of oil recovery agent in the stillage.

In some embodiments, the method of the invention includes treating and/or drying a de-oiled separated solids phase, which in some embodiments may be in the form of a de-oiled float, to produce distiller dry grains comprising the protein. Using methods known in the art, the de-oiled solids phase (e.g., de-oiled float) may be subjected to mechanical processes to remove non-protein dry mass prior to drying.

The method of the invention surprisingly and unexpectedly reduces the content of non-protein material recovered from the solids separated from stillage, e.g., in the separated solids phase. Thus, the method of the present invention provides for the efficient recovery from stillage of solids with an enriched protein content, e.g., having a high protein content based on the total weight of solids, e.g., relative to comparable methods that utilize inorganic coagulants to separate solids from stillage. Thus, the method of the present invention provides for the efficient production of distiller dry grain with an enriched protein content, e.g., a high protein content, based on the total weight of solids, relative to distiller dry grain produced by conventional methods The present invention also provides a composition comprising the dried/dry separated solids phase produced according to method of the invention, e.g., a composition comprising the protein-enriched distiller dry grain produced according to the method of the invention. The invention further provides a nutritional product comprising the protein-enriched dried/dry separated solids phase produced according to method of the invention, e.g., a nutritional product comprising the protein-enriched distiller dry grain produced according to the method of the invention. The invention moreover provides a livestock feed or fertilizer comprising the protein-enriched dried/dry separated solids phase produced according to method of the invention, e.g., livestock feed or fertilizer comprising the protein-enriched distiller dry grain produced according to the method of the invention.

The following aspects further illustrate the invention but, of course, should not be construed as in any way limiting its scope.

Aspects (1) In aspect (1) is presented a method of recovering protein from stillage produced in an ethanol production process, the method comprising:
  treating stillage comprising oil, protein, and water upstream of a separation, concentration or evaporation step with at least one organic coagulant and at least one flocculant, to produce a treated stillage comprising solids which include at least a portion of the oil and protein; and
  subjecting the treated stillage to a solid/liquid separation process, to produce a clarified stillage comprising a clarified aqueous phase and a separated solids phase, wherein the separated solids phase comprises at least a portion of the protein from the stillage.

(2) In aspect (2) is presented the method of aspect 1, wherein the stillage is whole stillage or thin stillage and the separated solids phase is in the form of a float layer.

(3) In aspect (3) is presented the method of aspect 1 or aspect 2, wherein the stillage is thin stillage and the separated solids phase is in the form of a float layer.

(4) In aspect (4) is presented the method of aspect 2 or aspect 3, comprising treating the thin stillage with the at least one organic coagulant and the at least one flocculant upstream of a concentration or evaporation step, to produce a treated thin stillage.

(5) In aspect (5) is presented the method of any one of aspects 2-4, further comprising separating at least a portion of the oil from the float to produce a de-oiled float.

(6) In aspect (6) is presented the method of aspect 5, further comprising drying the de-oiled float to produce distiller dry grain comprising the protein.

(7) In aspect (7) is presented the method of any one of aspects 1-6, wherein the organic coagulant comprises poly (diallyldimethylammonium chloride) (polyDADMAC), epichlorohydrin-diethylamine, dimethylamine, polyamines, polyquaternary amines, or a combination thereof.

(8) In aspect (8) is presented the method of any one of aspects 1-7, wherein the organic coagulant comprises polydiallyldimethylammonium chloride (polyDADMAC), epichlorohydrin-dimethylamine, or a combination thereof.

(9) In aspect (1) is presented the method of any one of aspects 1-8, wherein the at least one flocculant comprises an anionic flocculant.

(10) In aspect (10) is presented the method of aspect 9, wherein the anionic flocculant is a polymer comprising a monomer unit derived from a monomer selected from 2-acrylamido-2-methylpropane sulfonic acid ("AMPS"), 2-acrylamido-2-methylbutane sulfonic acid ("AMBS"), [2-methyl-2-[(1-oxo-2-propenyl)amino]propyl]-phosphonic acid, methacrylic acid, acrylic acid, salts thereof, and combinations thereof.

(11) In aspect (11) is presented the method of aspect 9 or aspect 10, wherein the anionic flocculant is a polymer comprising a monomer unit derived from acrylic acid.

(12) In aspect (12) is presented the method of any one of aspects 5-11, wherein the separating at least a portion of the oil from the float layer comprises treating the float layer with an oil recovery agent, which comprises a sorbitan ester of a fatty acid, an ethoxylated sorbitan ester of a fatty acid, or a combination thereof.

(13) In aspect (13) is presented the method of aspect 12, wherein the oil recovery agent comprises polyoxyethylene sorbitan monostearate.

(14) In aspect (14) is presented the method of any one of aspects 5-11, wherein the separating at least a portion of the oil from the float layer comprises treating the float layer with an oil recovery agent, which comprises a propylene glycol ester, a polyglycol ester, a polyglycerol fatty ester blend, a polyglycerol oleate ester, a block copolymer of ethylene oxide-propylene oxide polymer, a vegetable oil, a vegetable oil ethoxylate, or a combination thereof.

(15) In aspect (15) is presented the method of any one of aspects 5-11, wherein the separating at least a portion of the oil from the float layer comprises treating the float layer with an oil recovery agent, which comprises at least one surfactant and at least one hydrophilic silica.

(16) In aspect (16) is presented the method of any one of aspects 5-11, wherein the separating at least a portion of the oil from the float layer comprises treating the float layer with an oil recovery agent, which comprises a blend of 75-95% polysorbate 80, 5-15% hydrophobic precipitated silica, and ≤10% petroleum hydrocarbon; a blend of 75-95% castor oil ethoxylate, 5-15% hydrophobic precipitated silica, 10-30% vegetable oil, and ≤10% propylene glycol; or a blend of 75-95% polysorbate 80, 5-15% hydrophobic precipitated silica, and ≤10% PEG ester blend.

(17) In aspect (17) is presented the method of any one of aspects 5-11, wherein separating at least a portion of the oil from the float layer comprises heating and mechanical processing.

(18) In aspect (18) is presented the method of aspect 17, wherein the mechanical processing is performed with a decanter, a tricanter, a stacked disk centrifuge, or a combination thereof.

(19) In aspect (19) is presented the method of aspect 17 or aspect 18, wherein the mechanical processing is performed with a stacked disk centrifuge.

(20) In aspect (20) is presented the method of aspect 17, wherein the heating produces a temperature of from about 150° F. to about 220° F.

(21) In aspect (21) is presented the method of any one of aspects 1-20, wherein the solid/liquid separation process comprises dissolved air flotation, induced air flotation, or a combination thereof.

(22) In aspect (22) is presented an ethanol production process comprising the method of any one of aspects 1-21, wherein the ethanol production process is an ethanol biofuel process, a spirits distillery process, or a brewery process.

(23) In aspect (23) is presented the ethanol production process of any one of aspects 1-22, wherein the ethanol production process is an ethanol biofuel process.

(24) In aspect (24) is presented the ethanol production process of aspect 22 or aspect 23, wherein the ethanol biofuel production process is a wet milling process or a dry grind process.

(25) In aspect (25) is presented the ethanol production process of any one of aspects 22-24, wherein the ethanol biofuel production process is a dry grind process.

(26) In aspect (26) is presented distiller dry grain produced according to any one of aspects 6-25.

(27) In aspect (27) is presented a nutritional product comprising the distiller dry grain of aspect 26.

(28) In aspect (28) is presented a livestock feed or fertilizer comprising the distiller dry grain of aspect 26.

(29) In aspect (29) is presented the method of any one of aspects 1-5, further comprising drying the separated solids phase to produce dried grains.

(30) In aspect (30) is presented a nutritional product comprising the dried grains of aspect 29.

(31) In aspect (31) is presented a livestock feed or fertilizer comprising the dried grains of aspect 29.

The following examples further illustrate the invention but, of course, should not be construed as in any way limiting its scope.

Example 1

This example demonstrates typical protein recovery from thin stillage in a dry grind ethanol plant, after treatment of the thin stillage with anionic flocculant in the GEM process, as in FIG. 1.

TABLE 1

GEM Protein Recovery from Thin Stillage in an Ethanol Plant

| | GEM Protein Recovery |
|---|---|
| Experiment 1 | 36.68% |
| Experiment 2 | 33.03% |
| Experiment 3 | 31.65% |
| Average | 33.79% |
| Stand. deviation | 2.60% |

GEM Protein concentration was measured using a combustion method (AOAC 990.03). The nitrogen value is multiplied by a factor of 6.25 and that value reported as crude protein. Protein recovery was calculated as ((% protein in thin stillage % protein in GEM effluent)/% protein in thin stillage) %.

This reference example demonstrates that, on average, less than 34% of possible protein was recovered from thin stillage after prior art treatment with anionic flocculant in the GEM process.

Example 2

This example demonstrates the percentage of protein % dry weight in samples from along the process stream collected in the ethanol plant of Example 1.

TABLE 2

Percentage Protein in Dry Weight of Samples Recovered at Points Along the Process Stream in an Ethanol Plant

| Plant samples | Protein Dry Weight % |
|---|---|
| Thin Stillage | 27.1 |
| GEM Float | 26.5 |
| De-oiled float | 42.1 |

Dry weight protein concentration was measured using a combustion method (AOAC 990.03) to obtain the amount of nitrogen, as in Example 1. Dry matter was calculated from moisture data which was measured using AOAC 969.35. Samples are placed in aluminum tins and dried in a 60 or 70 degrees C. vacuum oven (20-25 mm Hg) for 4 or 18 hours, with or without digested pure quartz sand. Loss in mass is reported as moisture.

This reference example demonstrates that, at about 33% protein recovery in the GEM float (see Table 1), after the de-oiled process in the plant, the protein concentration is only 42%.

Example 3

This example demonstrates the percent protein recovery from thin stillage treated with anionic flocculent and different coagulant chemistries.

Unlike the field testing performed in previous examples, the present example represents laboratory data gathered using a jar test. The procedure was as follows: first, a sample of untreated room temperature thin stillage was poured into a beaker (e.g., 500 mL). While mixing at 200 rpm, coagulant was added (or nothing was added if sample was only treated with flocculant), and the sample was mixed for 60 sec. The mixing rate was lowered to 100 rpm and anionic flocculant solution was added and mixed for 30 sec, followed by slow mixing at 50 rpm for 2 mins. Mixing was stopped, and the sample allowed to settle for 30 mins. Finally, the supernatant was removed, and the turbidity and protein concentrations were measured. The amount of flocculant was fixed for all jar tests run in an Example, while the amount of coagulant varied for each coagulant chemistry to obtain the dosage curve.

The total percent protein recovery in the settled solid phase which simulates the GEM float in the field was determined after samples of thin stillage were treated with a fixed amount of the same anionic flocculant and the indicated coagulant at the indicated amount. Organic nitrogen was used to represent the amount of protein in the samples. Organic nitrogen=Total Kjeldahl Nitrogen (TKN, U.S. EPA method 351.2R2.0)–Ammonia (U.S. EPA method 350.1R2.0). Total percent protein recovery was calculated as: 100%–(amount of organic nitrogen in supernatant of each treated sample/amount of organic nitrogen in untreated thin stillage sample) %.

Figure 5:
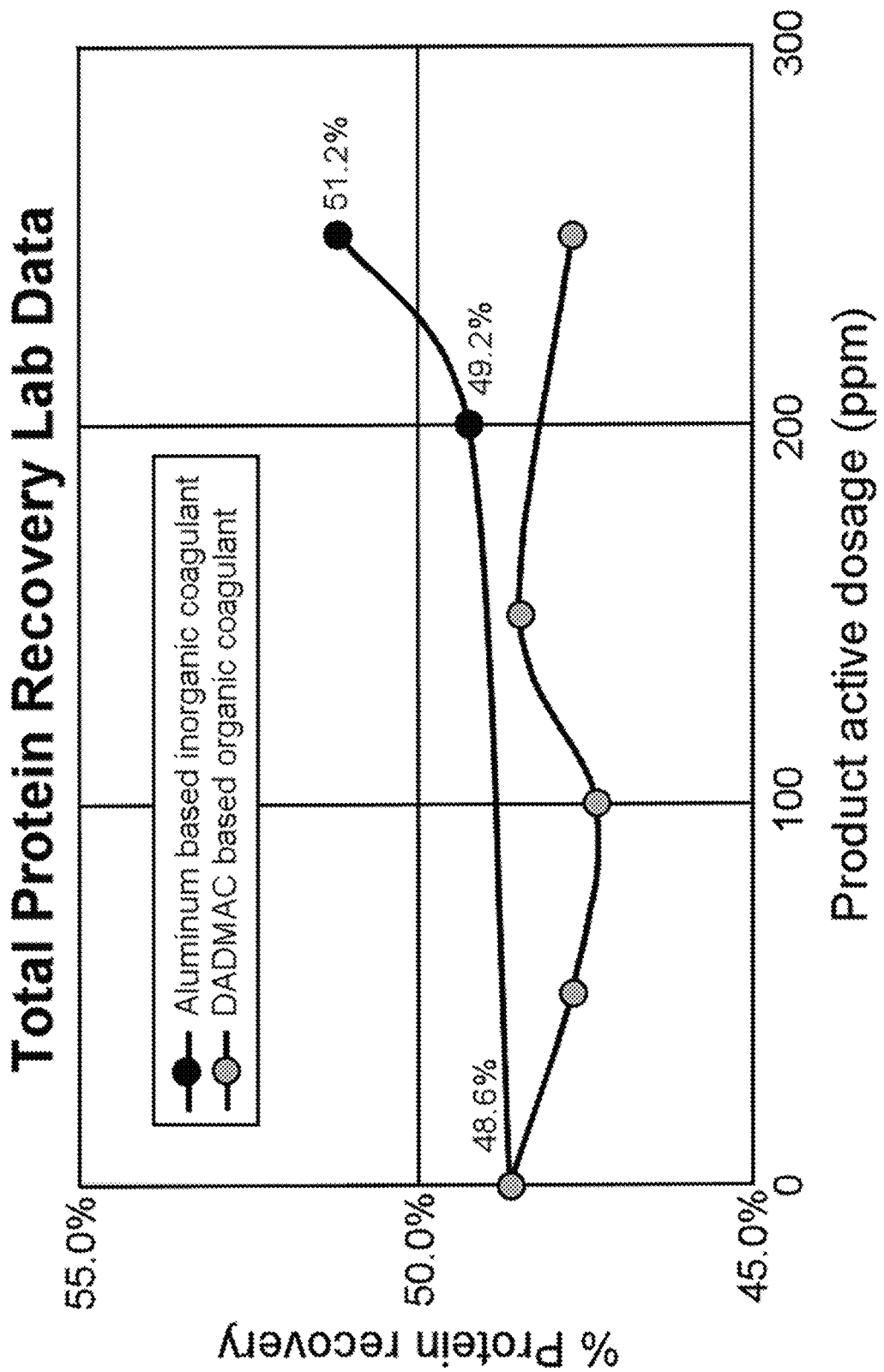
FIG. 5 depicts a graph illustrating total protein recovery dosage curves from thin stillage treated with a flocculant and a representative inorganic or organic coagulant in a lab test.
Figure 6:
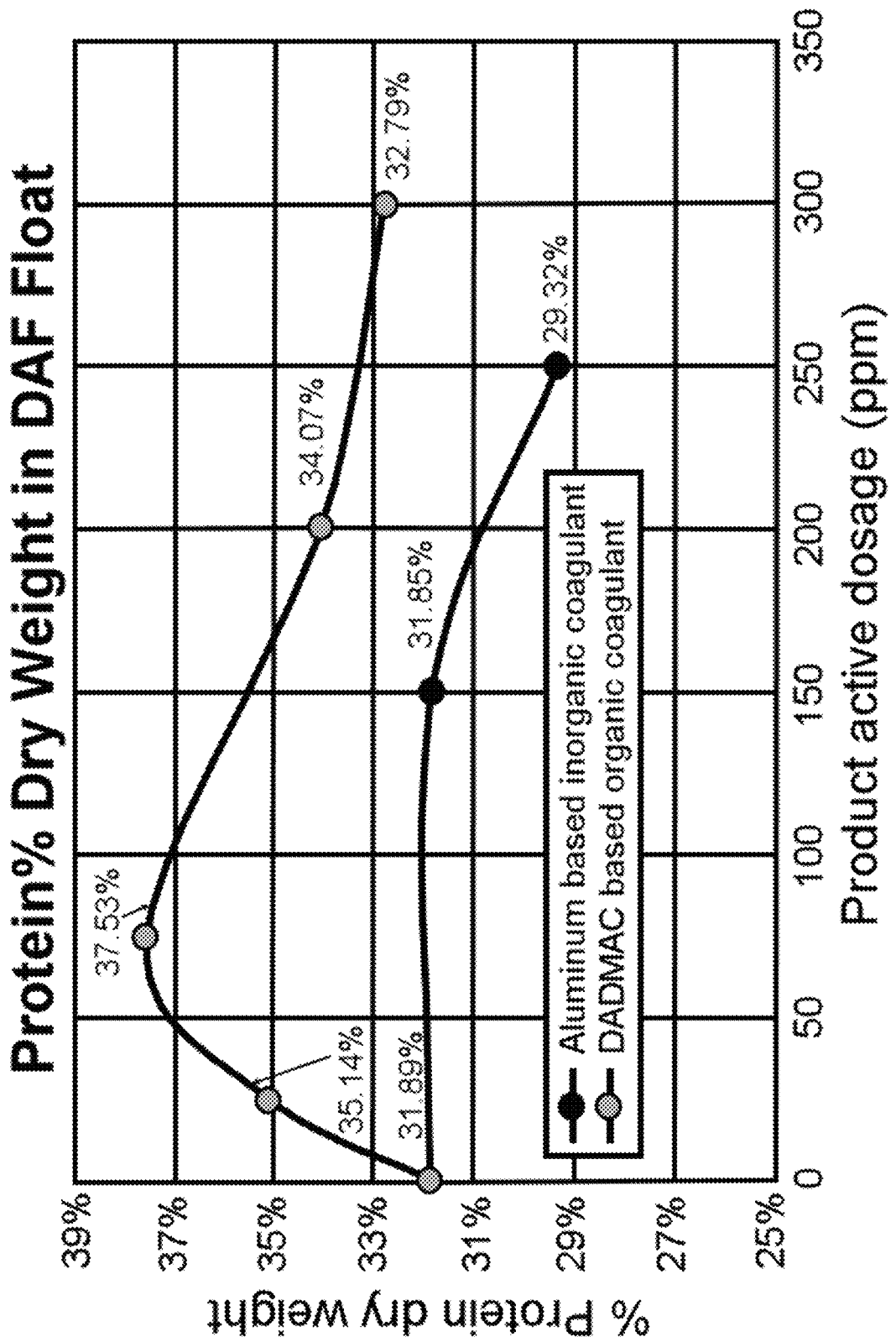
FIG. 6 depicts a graph illustrating dry weight percent protein recovery from thin stillage treated with a flocculant and a representative inorganic or organic coagulant in a lab test.
Figure 7:
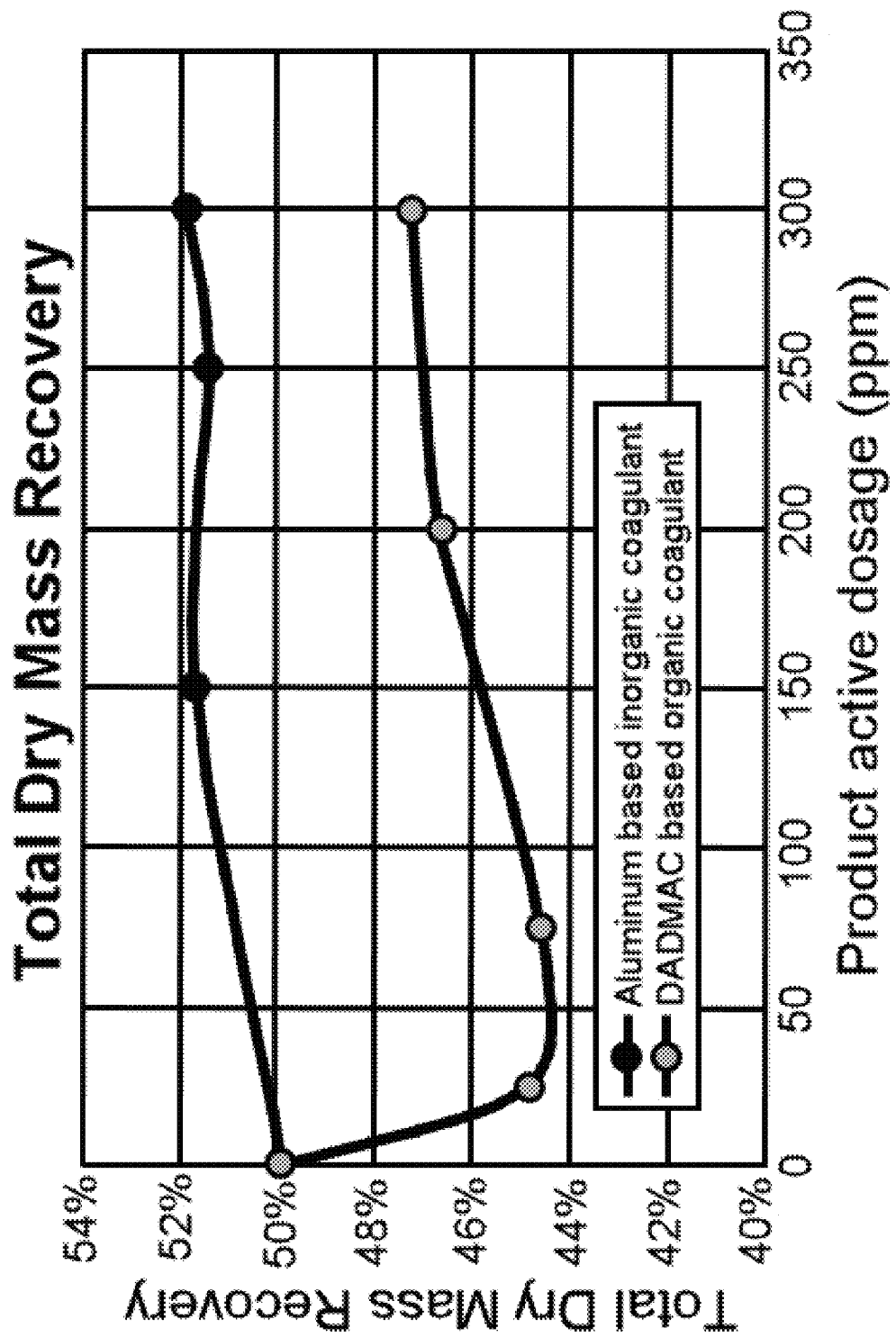
FIG. 7 depicts a graph illustrating total dry mass recovery from thin stillage treated with a flocculant and a representative inorganic or organic coagulants in a lab test.

The amount of flocculant was fixed at 30 ppm for all jar tests, while the amount of coagulant was varied for each coagulant chemistry to obtain a dosage curve. The flocculant used in all Examples was GR-109, a high molecular weight inverse-phase emulsion consisting of ~25% polymer solids of polyacrylamide/acrylate. The representative inorganic coagulant used was either Ultrion 8187 (aluminum chlorophydate) or Nalco 2 (sodium aluminum). The representative organic coagulant used was GR308 poly(diallyldimethylammonium chloride; DADMAC) in all examples. For each type of coagulant, a dosage curve was prepared, with representative examples of dosage curves shown in the graph in FIG. 5. FIG. 5 depicts the dosage curves for total protein recovery in samples treated with a flocculant and either inorganic or organic coagulants. FIG. 6 depicts the dosage curves for percentage protein as dry weight of the settled solid phase in the jar test which simulates the GEM float in the field from thin stillage treated with flocculant and either inorganic or organic coagulants. FIG. 7 depicts the dosage curves for total dry weight recovered to the settled solid phase from thin stillage treated with flocculant and either inorganic or organic coagulants.

As shown in the graph depicted in FIG. 5, addition of inorganic coagulant to the flocculant treated sample was found to increase total protein recovery compared to treatment with flocculant alone (active dosage at zero coagulant added), while the organic coagulant did not demonstrate improved total protein recovery. In contrast, addition of inorganic coagulant did not increase the protein percentage of dry matter in the settled solid phase, i.e, the protein content in the dried solid phase which simulates the dried GEM float in field, as shown in the graph in FIG. 6. Unexpectedly, organic coagulant did significantly increase the protein content in the dried solid phase. This discrepancy can be explained by the different results found in total dry mass recovery between inorganic and organic coagulants. As shown in the graph depicted in FIG. 7, inorganic coagulant captured more total dry mass than flocculant alone, while organic coagulant captured less. Thus, inorganic coagulant captured not only protein but also a significant amount of other dry mass into the solid phase, which as a result diluted the protein dry weight concentration in the solid phase. In contrast, organic coagulant selectively captured protein over other dry mass, so the relative protein concentration as a percentage of dry matter in the solid phase was increased for organic coagulant.

Example 4

The same phenomena demonstrated in the lab were also observed in field trials.

The field trials were conducted in a dry grind ethanol plant in Illinois. The indicated coagulant at the indicated amount was mixed inline with the thin stillage stream at the plant operating temperature of 180° F. to 200° F., followed by an anionic flocculant at a fixed dosage of 40 ppm before the stream traveled into the GEM (Gas Energy Mixing System). Both thin stillage and GEM float samples were taken after each coagulant/flocculant dosage. Dry weight protein concentration and total dry mass were determined as in Example 2. Total protein % recovery or dry mass % recovery in the field trial was calculated as:

(flow of GEM float)*(protein % dry weight or % dry mass in GEM float)/(flow of thin stillage)*(protein % dry weight or % dry mass in thin stillage.

Figure 8:
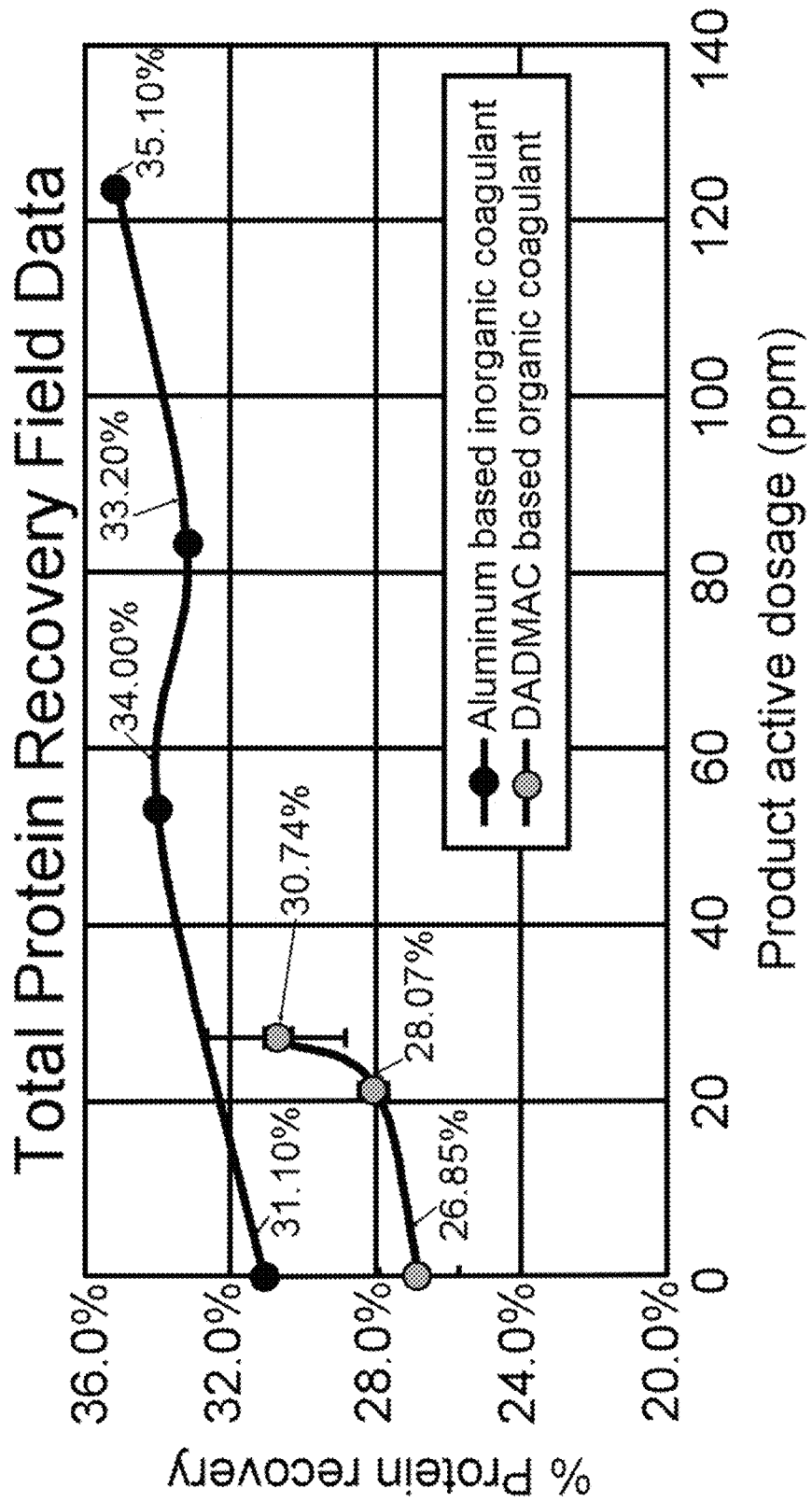
FIG. 8 depicts a graph illustrating total protein recovery dosage curves from thin stillage treated with a flocculant and a representative inorganic or organic coagulant in a field test.
Figure 9:
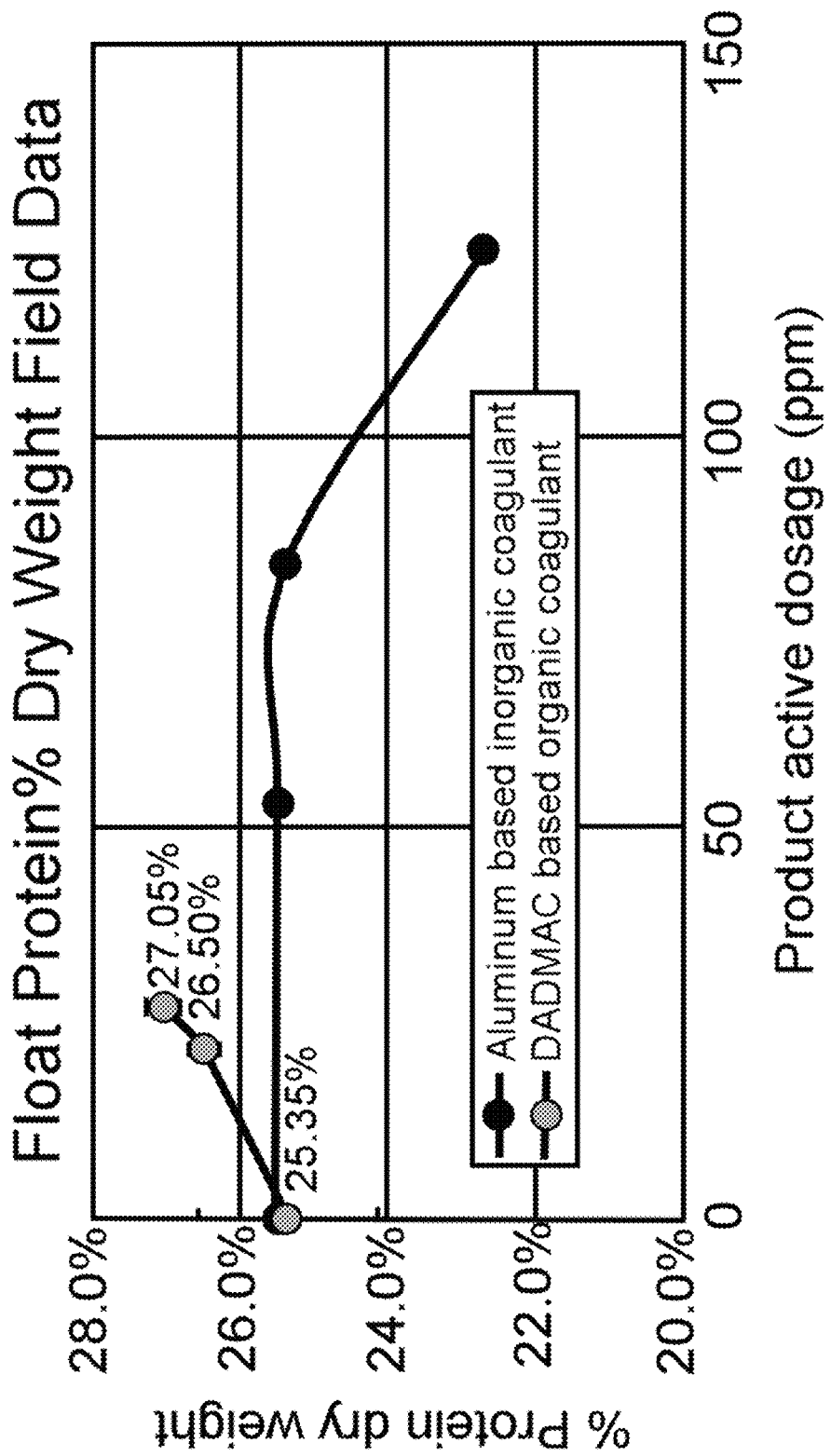
FIG. 9 depicts a graph illustrating dry weight percent protein recovery from thin stillage treated with flocculant and a representative inorganic or organic coagulant in a field test.
Figure 10:
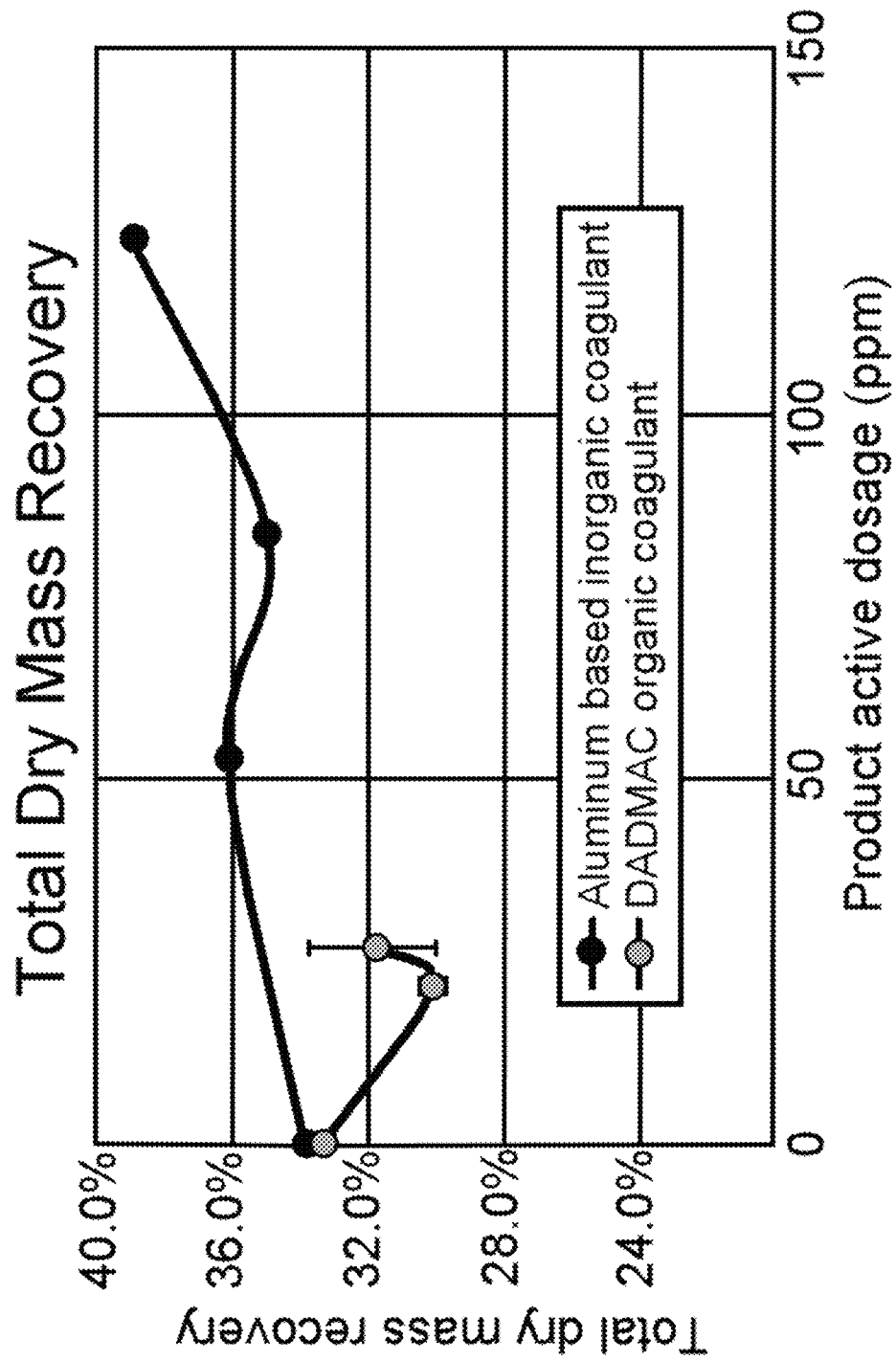
FIG. 10 depicts a graph illustrating total dry mass recovery from thin stillage treated with a flocculant and a representative inorganic or organic coagulant in a field test.

As demonstrated in the graphs depicted in FIGS. 8 and 9, addition of both inorganic and organic coagulant increased total protein recovery in the thin stillage GEM process. However, inorganic coagulant did not increase the percentage protein dry weight in the GEM float. In contrast, as in the jar test, the organic coagulant did increase the % protein dry weight in the GEM float. The results shown in FIGS. 8 and 9 are explained by the graph depicted in FIG. 10, which demonstrates that the inorganic coagulant captures more total dry mass than the organic coagulant.

The field trial data verify that organic coagulant can selectively recover protein over other dry mass recovered from the stillage process stream in an ethanol production process, which can increase the percentage protein in the dry weight in the float. Protein enrichment in the dried and/or dry grains product, e.g., distiller dry grain, increases the value of the product.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of recovering protein from stillage produced in an ethanol production process, the method comprising:
    treating stillage comprising oil, protein, and water upstream of a separation, concentration or evaporation step with about 50 ppm to about 500 ppm of a coagulant comprising poly(diallyldimethylammonium chloride) (polyDADMAC), epichlorohydrin-diethylamine, or a combination thereof, and about 50 ppm to about 500 ppm of a polymer comprising a monomer unit derived from a monomer selected from 2-acrylamido-2-methylpropane sulfonic acid ("AMPS"), 2-acrylamido-2-methylbutane sulfonic acid ("AMBS"), [2-methyl-2-[(1-oxo-2-propenyl)amino |propyl]-phosphonic acid, methacrylic acid, acrylic acid, salts thereof, and combinations thereof, to produce a treated stillage comprising solids which include at least a portion of the oil and protein; and subjecting the treated stillage to a solid/liquid separation process, to produce a clarified stillage comprising a clarified aqueous phase and a separated solids phase, wherein the separated solids phase comprises at least a portion of the protein from the stillage,
    wherein the stillage is whole stillage or thin stillage and the separated solids phase is in the form of a float layer and
    the method further comprising separating at least a portion of the oil from the float layer to produce a de-oiled float layer by treating the float layer with an oil recovery agent, comprising a blend of 75-95% castor oil ethoxylate, 5-15% hydrophobic precipitated silica, 10-30% vegetable oil, and <10% propylene glycol.

2. The method of claim 1, comprising treating the thin stillage with the coagulant and the polymer upstream of the concentration or the evaporation step, to produce a treated thin stillage.

3. The method of claim 1, further comprising drying the de-oiled float layer to produce distiller dry grain comprising the protein.

4. The method of claim 1, wherein the solid/liquid separation process comprises dissolved air flotation, induced air flotation, or a combination thereof.

5. The method of claim 1, wherein the separating at least a portion of the oil from the float layer comprises heating and mechanical processing.

6. An ethanol production process comprising the method of claim 1, wherein the ethanol production process is an ethanol biofuel process, a spirits distillery process, or a brewery process.

7. The method of claim 1, further comprising drying the separated solids phase to produce dried grains.

* * * * *